United States Patent [19]

Klemm et al.

[11] 4,034,093
[45] July 5, 1977

[54] 4(1H)-PYRIMIDINONES

[75] Inventors: Kurt Klemm, Allensbach; Erhard Langenscheid, Konstanz, both of Germany

[73] Assignee: Byk Gulden Lomberg Chemische Fabrik GmbH, Konstanz, Germany

[22] Filed: Sept. 4, 1973

[21] Appl. No.: 393,814

[30] Foreign Application Priority Data

Sept. 8, 1972 Luxembourg .......................... 66036
Sept. 8, 1972 Luxembourg .......................... 66037
Sept. 8, 1972 Luxembourg .......................... 66038

[52] U.S. Cl. ..................... 424/251; 260/247.1 M; 260/247.2 A; 260/256.4 C; 260/256.5 R; 424/248.51; 424/248.52; 424/248.5; 424/248.54
[51] Int. Cl.$^2$ ............. C07D 239/22; A61K 31/535
[58] Field of Search ............ 260/256.4 C, 247.1 M, 260/247.2 A

[56] References Cited

UNITED STATES PATENTS 2,831,833   4/1958   Aycock et al. ............. 260/256.4 C

OTHER PUBLICATIONS

Kloetzer et al., "Chemical Abstracts," vol. 66, 1967, Col. 46390t, (Abstract of Montash. Chem., vol. 96(6), 1965, pp. 1731–1738).

Primary Examiner—Donald G. Daus
Assistant Examiner—James H. Turnipseed
Attorney, Agent, or Firm—Berman, Aisenberg & Platt

[57] ABSTRACT

Therapeutically-active and pharmacologically-acceptable 1-amido-5-cyano-4(1H)-pyrimidinones and their pharmaceutically-acceptable acid addition salts inhibit xanthineoxidase and are useful as the active ingredient in medicaments for the treatment of gout. Such pyrimidinones are prepared by treating 2-(acyl) hydrazonomethyl-3-chloro or hydroxy-4-aza-2,4-pentadienenitriles with acid.

23 Claims, No Drawings

4(1H)-PYRIMIDINONES

RELATED APPLICATIONS

This application is related to three concurrently-filed applications of the subject inventors. These applications are entitled FORMYLAZAPENTADIENENITRILES (U.S. Pat. No. 3,944,667) 3-CHLORO-2-HYDRAZONOMETHYL-4-AZA-2,4-PENTADIENENITRILES (U.S. Pat. No. 393,812, now abandoned) and 2-HYDRAZONOMETHYL-3-HYDROXY-4-AZA-2,4-PENTADIENENITRILES (U.S. Pat. No. 3,923,817) The disclosure of each of these related applications is incorporated herein, in its entirety, by reference.

BACKGROUND

Derivatives of pyrazolo-(3,4-d)-pyrimidine which have enzyme inhibiting properties have been known for a considerable time. 4-hydroxy-1H-pyrazolo-(3,4-d)-pyrimidine, known as "allopurinol", inhibits the enzyme, xanthineoxidase. This enzyme catalyses the oxidation of purine derivatives to uric acid in vivo. In a similar manner allopurinol suppresses the oxidation of 6-mercaptopurine to 6-thiouric acid (German Offenlegungsschrift No. 1,904,894). Since allopurinol considerably reduces the amount of uric acid formed in purine metabolism, it is used therapeutically for treating gout. A disadvantage of so using allopurinol is, however, that it has relatively high toxicity and, in comparison with its toxicity, is used in relatively high doses, i.e. at the rate of 100 to 800 mg per person per day. It has thus been desirable to find products which, while having a substantially lesser degree of toxicity, also inhibit xanthineoxidase and are useful for treating gout.

SUMMARY 1-(organic-acid-acyl)amino-5-cyano-4-(1H)-pyrimidinones, an acid addition salt thereof (preferably one which is pharmacologically acceptable) or an acid amide or other functional derivative thereof, particularly a compound of the formula

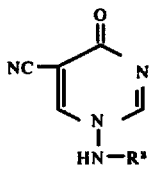

wherein
R$^3$ is an organic acid acyl, e.g. —C(X)—R$^4$, —C(X)—Y—R$^4$ and —C(X)—N(R$^5$)R$^6$;
R$^4$ is a hydrogen atom (—H), alkyl, alkenyl or alkynyl having from 1 to 14 carbon atoms, substituted or unsubstituted alkoxyalkyl or alkenyloxyalkyl having up to 13 carbon atoms, substituted or unsubstituted cycloalkyl having from 3 to 6 ring carbon atoms, substituted or unsubstituted phenyl or nuclearly-substituted or unsubstituted phen(lower-)alkyl; any substituent of substituted alkenyloxyalkyl or substituted alkoxyalkyl being a salt-forming group, such as —NR$^5$R$^6$; any substituent or substituted cycloalkyl being lower alkyl or a salt-forming group, such as —NR$^5$R$^6$; any substituent of substituted phenyl or of substituted phenalkyl being lower alkyl, lower alkoxy, lower alkylmercapto, alkoxycarbonyl with from 2 to 5 carbon atoms, halo (chloro, fluoro, bromo or iodo), trifluoromethyl, nitro and/or cyano;
R$^5$ is a hydrogen atom (—H), lower alkyl, lower alkoxyalkyl having from 2 to 6 carbon atoms, cycloalkyl with from 3 to 6 ring carbon atoms or, together with R$^6$, alkylene having from 2 to 5 carbon atoms or a divalent aliphatic chain having from 3 to 5 chain members, each of at least two of which is methylene or another lower alkylidene and at least one remaining chain member is, independently, —O—, —S—, or —N(R$^7$)—;
R$^6$ is a hydrogen atom (—H), lower alkyl, lower alkoxyalkyl having from 2 to 6 carbon atoms, cycloalkyl with from 3 to 6 ring carbon atoms or, together with R$^5$, alkylene having from 2 to 5 carbon atoms or a divalent aliphatic chain having from 3 to 5 chain members, each of at least two of which is methylene or another lower alkylidene and at least one remaining chain member is, independently, —O—, —S—, or —N(R$^7$)—;
R$^7$ is a hydrogen atom (—H) or lower alkyl, preferably with from 1 to 5 carbon atoms and more particularly, methyl;
X is =O, =S (each of which is a chalogen having an atomic number from 8 to 16, inclusive) or =NR$^7$, preferably =O;
Y is —S—or —O—, preferably —O—;
and acid addition salts thereof, are useful, e.g. in pharmaceutically-acceptable conventional oral dosage forms, for treating gout. Such compounds are prepared, e.g., by treating, with or without heating, a substituted 3-chloro or hydroxy-2-hydrazonomethyl-4-aza-2,4-pentadienenitrile of one of the formulae

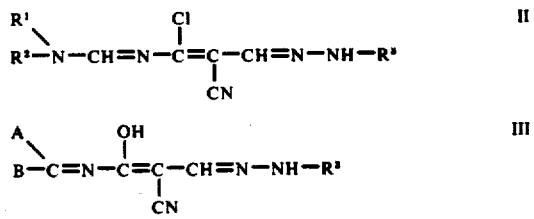

or its tautomeric form or salt with an organic or inorganic acid,
wherein
R$^1$ is lower alkyl, cycloalkyl with from 3 to 6 ring carbon atoms, or together with R$^2$, alkylene having from 2 to 5 carbon atoms, preferably pentamethylene, or a divalent aliphatic chain having from 3 to 5 chain members, each of at least two of which is methylene or another lower alkylidene and at least one remaining chain member is, independently, —O—, —S— or —N(R$^7$)—, e.g. 3-aza-, 3-thia- or, preferably, 3-oxa-pentamethylene;
R$^2$ is lower alkyl, cycloalkyl with from 3 to 6 ring carbon atoms or, together with R$^1$, alkylene having from 2 to 5 carbon atoms, preferably pentamethylene, or a divalent aliphatic chain having from 3 to 5 chain members, each of at least two of which is methylene or another lower alkylidene and at least one remaining chain member is, independently, —O—, —S— or —N(R$^7$)—, e.g. 3-aza-, 3-thia- or, preferably, 3-oxa-pentamethylene;
R$^3$ has its previously-ascribed meaning;
R$^7$ has its previously-ascribed meaning;

A is a hydrogen atom (—H), hydroxyl (—OH),

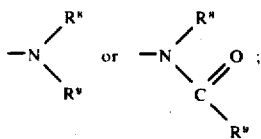

B is different from A, but is one of the meanings ascribed to A;

$R^7$ is a hydrogen atom (—H) or lower alkyl; $R^8$ is hydrogen atom (—H), lower alkyl, lower alkoxyalkyl, cycloalkyl or methyl-substituted cycloalkyl with from 3 to 6 ring carbon atoms or, together with $R^9$, alkylene having from 2 to 5 carbon atoms, preferably pentamethylene, or a divalent aliphatic chain having from 3 to 5 chain members, each of at least two of which is methylene or another lower alkylidene and at least one remaining chain member is, independently, —O—, —S— or —N($R^7$)—, such as 3-thia, 3-aza- or, preferably, 3-oxapentamethylene;

$R^9$ is a hydrogen atom (—H), lower alkyl, lower alkoxyalkyl, cycloalkyl or methyl-substituted cycloalkyl with from 3 to 6 ring carbon atoms, or, together with $R^8$, alkylene having from 2 to 5 carbon atoms, preferably pentamethylene, or a divalent aliphatic chain having from 3 to 5 chain members, each of at least two of which is methylene or another lower alkylidene and at least one remaining chain member is, independently, —O—, —S— or —N($R^7$)—, such as 3-thia-, 3-aza- or, preferably, 3-oxapentamethylene;

with an organic or inorganic acid. Another method of preparation of the compounds of formula I comprises reacting a compound of the general formula IV

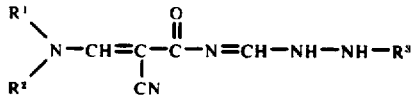

or its tautomeric form or its salt with an organic or inorganic acid, in which $R^1$, R2, $R^3$ have the same meanings given in the general formula II, with an inorganic or organic acid.

A further method of preparation of compounds of formula I comprises reacting cyanoacetamide with a trialkyl orthoformate or a dialkoxymethyl ester of an organic carboxylic acid in the presence of an acid anhydride and reacting the resulting reaction product with a hydrazine derivative $R^3$—NH—$NH_2$, in which $R^3$ has the same meaning as given in the general formula I.

Any obtained free compound with a salt-forming group is, optionally, converted by conventional means into one of its acid addition salts, more particularly a pharmacologically-acceptable acid addition salt, or any resultant acid addition salt is conventionally converted, if desired, into another acid addition salt, e.g., a therapeutically-compatible salt, or into the corresponding free base.

DETAILS

The starting materials of formula II are described in the concurrently-filed and previously-noted application Ser. No. 393,812; those of formula III are described in U.S. Pat. No. 3,923,817.

3-Chloro-2-(organic-acid-acyl-substituted)hydrazonomethyl-5-(tertiary)amino or cycloimino-4-aza-2,4-pentadienenitriles of formula II and acid addition salts thereof are prepared by reacting a corresponding 4-aza-3-chloro-2-formyl-5-(tertiary)amino or cycloimino-2,4-pentadienenitrile or an acid addition salt thereof with an acyl hydrazine, $R^3$—NH—$NH_2$, wherein $R^3$ has its previously-ascribed meaning. The reaction is preferably carried out in an inert organic solvent, e.g. benzene, toluene, xylene, dioxane, ethyl acetate, chloroform, dimethylformamide or an alcohol, such as ethanol or isopropanol, or solvent mixture while cooling or at an elevated temperature, preferably at temperatures between 0° and 100° C or at the boiling temperature of the solvent, more particularly between 20° and 60° C.

2-(organic-acid-acyl-substituted)hydrazonomethyl-3-hydroxy-5-[hydroxy, (lower)alkoxy, amino, amido, cycloimino] or cycloimido-4-aza-2,4-pentadienenitrile of formula III, tautomers and acid addition salts thereof are prepared, e.g., by reacting a corresponding 5-hydroxy, amino, amido, cycloimino or cycloimido-4-aza-2-formyl-3-hydroxy-2,4-pentadienenitrile with an acyl hydrazine, $r^3$—NH—$NH_2$, wherein $R^3$ has its previously-ascribed meanining. This reaction is preferably carried out in an inert organic solvent, e.g. chloroform, benzene, toluene, xylene, dioxane, dimethylformamide or acetyl acetate, with cooling or at an elevated temperature, for example at the boiling point of the solvent, preferably at room temperature.

Starting materials of formula IV are obtained by reacting a compound of the formula

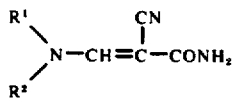

in which $R^1$ and $R^2$ have the meanings given for formula IV, with an trialkyl orthoformate, for example triethyl orthoformate, or a dialkoxymethyl acetate, for example diethoxymethyl acetate, in the presence of an acid anhydride, for example acetate anhydride; the resulting reaction product is reacted with a hydrazine derivative of the formula $H_2N$—NH—$R^3$, in which $R^3$ has its previously-ascribed meaning. The reaction of V with trialkyl orthoformate or dialkoxymethyl acetate is carried out in the presence, preferably in the absence, of inert organic solvents, and preferably at temperatures between 50° to 150° C. The reaction of V with a trialkyl orthoformate is preferably carried out in the presence of at least equimolar quantities of acid anhydride; the reaction of V with a dialkoxymethyl acetate is preferably carried out in the presence of at least catalytic quantities of acid anhydride, and the orthoester or dialkoxymethyl acetate is preferably used in an excess, and more particularly in a twofold to fourfold molar amount relative to the amount of V.

Compounds of formula V are prepared according to the method disclosed in the Belgian Pat. No. 727,754 or by heating of cyanacetamide with formamide acetals of the formula $R^1(R^2)NCH(OR)_2$, wherein $R^1$ and $R^2$ have the above mentioned meanings and R represents and alkyl group having from 1 to 7, preferably 1 to 4 carbon atoms, at about 50° C in a molar ratio of formamide acetal: cyanacetamide of about 1:1.

Throughout this disclosure and that for the previously-identified related applications a number of terms reappear. The following retain the same meanings throughout the four applications unless expressly further limited:

alkyl — both straight-chain and branch-chain saturated hydrocarbon radicals having a single available bond and containing from 1 to 14 carbon atoms unless otherwise limited, e.g. methyl, ethyl, propyl, isopropyl, butyl, isobutyl, secondary butyl, tertiary butyl, pentyl, isopentyl, 1- or 2-methylbutyl, tertiary pentyl, hexyl, isohexyl, 1-, 2- or 3-methylpentyl, 1-, 2- or 3-ethylbutyl, 1,2-, 1,3- or 2,3-dimethylbutyl, heptyl, isoheptyl and dodecyl;

alkenyl — both straight-chain and branch-chain mono- or poly-olefinically-unsaturated, preferably not more than di-olefinically-unsaturated, hydrocarbon radicals having a single available bond, having no triple bonds and containiang from 2 to 14 carbon atoms unless otherwise limited, e.g. vinyl, allyl, 2-methylallyl, propene-1yl, butene-1- or 2-yl, 2-methylpropene-1-yl, pentene-1-, 2-, 3- or 4-yl, hexene-1-, 2-, 3-, 4- or 5-yl, heptene-1-, 2-, 3-, 4-, 5- or 6-yl and pentadiene-1,4-, 1,3- or 2,4-yl;

alkenyloxyalkyl — alkenyloxy-substituted alkyl wherein both alkenyl and alkyl are as previously defined unless otherwise limited, e.g. allyloxyethyl;

alkinyl or alkynyl — both straight-chain and branch-chain unsaturated hydrocarbon radicals having at least one triple bond and from 2 to 14 carbon atoms, e.g. propine-1- or 3-yl;

alkoxy — all alkyl-oxy radicals wherein the alkyl is as previously defined e.g. methoxy, ethoxy, propoxy, isopropoxy, butoxy, isobutoxy, secondary butoxy and tertiary butoxy;

lower — restricts the radical to which it is applied to at most 7 carbon atoms and preferably at most 4 carbon atoms, unless specifically more limited;

lower alkoxyalkyl — monovalent radicals having at most six carbon atoms, e.g. ethoxyethyl, methoxyethyl and ethoxymethyl;

cycloalkyl — with methyl-substituted cycloalkyl, such monovalent hydrocarbon rings as cyclopropyl, cyclopentyl, 2- or 3-methylcyclopentyl and, preferably, cyclohexyl;

alkylmercapto — an alkyl thiol lacking the thiol hydrogen and in which the alkyl is as previously defined, e.g. methylmercapto, ethylmercapto, propylmercapto, isopropylmercapto and butylmercapto;

phen(lower)alkyl — phenyl-substituted alkyl wherein the alkyl has from 1 to 4, preferably 1 or 2, carbon atoms, e.g. 1- or 2-phenethyl and, preferably, benzyl;

alkylene having from 2 to 5 carbon atoms — straight-chain or branched-chain saturated hydrocarbon radical having two available bonds emanating from different carbon atoms, e.g. ethylene, trimethylene, 1- or 2-methylethylene, tetramethylene, 1-, 2- or 3-methyltrimethylene, 1- or 2-ethylethylene and pentamethylene;

divalent aliphatic chain — a divalent chain having at least two chain carbon atoms, at least one chain hereto atom and available bonds emanating from different chain atoms, e.g. 2-oxapropylene, 3-thiabutylene, 2-methyl-2,4-diazapentylene, 2-aza-4-oxapentylene, 2-methyl-3-oxapentylene or 3-thiapentylene, preferably 3-oxapentylene;

alkylidene — a divalent saturated hydrocarbon radical having 2 to 4 carbon atoms and two available bonds emanating from the same carbon atom, e.g. ethylidene, propylidene, butylidene;

alkoxycarbonyl — carbonyl substituted by alkoxy as previously defined, e.g. methoxycarbonyl, ethoxycarbonyl, propoxycarbonyl, isopropoxycarbonyl, butoxycarbonyl and isobutoxycarbonyl;

organic acid acyl or acid amide — acyl or amide based on any organic acid for example —CO—R$^4$, —CS—R$^4$, —C(NR$^7$)—R$^4$, —CO—O—R$^4$, —CO—S—R$^4$, —CS—O—R$^4$, —CS—S—R$^4$, —C(NR$^7$)—O—R$^4$, —C(NR$^7$)—S—R$^4$, —CO—N(R$^5$)R$^6$, —CS—N(R$^5$)R$^6$ and —C(NR$^7$)—N(R$^5$)R$^6$, wherein each of R$^4$, R$^5$, R$^6$ and R$^7$ has its previously-ascribed meaning;

substituted — mono- or poly-substituted by the same or different contemplated substituents;

acid addition salts or salts with organic or inorganic acids — a salt formed by a salt-forming group, such as a tertiary amine, and an acid, wherein the acid is, for example, an organic acid, e.g. tartaric acid; an inorganic acid, e.g. hydrochloric acid, hydrobromic acid and sulfuric acid; a monobasic acid, such as an alkanesulfonic acid, e.g. methanesulfonic acid (H$_3$C—SO$_3$H); a dibasic acid, e.g. succinic acid; a tribasic acid, e.g. phosphoric acid and citric acid; a saturated acid, e.g. acetic acid; an ethylenically-unsaturated acid, e.g. maleic acid and fumaric acid; and an aromatic acid, e.g. salicylic acid and arylsulfonic acids, such as benzenesulfonic acid; preferred acid addition salts are those which are physiologically-acceptable; all references to organic or inorganic acids include the entire scope thereof unless otherwise limited.

Compounds of this invention which have particularly noteworthy properties are therapeutically-active and pharmacologically-compatible compounds of the formula

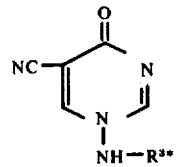

I* wherein
R$^{3=}$ is —CO—R$^{4=}$, —CO—OR$^{4=}$ or, moreover, —CO—N(R$^{5=}$)R$^{6=}$ or —C(NH)—N(R$^{5=}$)R$^{6=}$; R$^{4=}$ is alkyl having from 1 to 14, preferably from 1 to 7, carbon atoms; substituted or unsubstituted alkoxyalkyl having from 2 to 13, preferably from 2 to 6, carbon atoms; substituted or unsubstituted alkenyloxyalkyl having up to 13, preferably from 5 to 7, carbon atoms; substituted or unsubstituted phenyl; nuclearly-substituted or unsubstituted benzyl; substituted or unsubstituted cycloalkyl with from 3 to 6 ring carbon atoms, preferably a cyclohexyl radical; any substituent on a substituted alkyl, substituted alkoxyalkyl, substituted cycloalkyl (other than a methyl group) being a salt-forming basic group, particularly an —N(R$^{5=}$)R$^{6=}$ group; any substituent on a substituted phenyl or on a substituted benzyl being lower alkyl, lower alkoxy, lower alkylmercapto, alkoxycarbonyl with from 2 to 5 carbon atoms, halo, trifluoromethyl, nitro or cyano; and each of $R^{5-}$ and $R^{6-}$ is, independently, a hydrogen atom (—H) or alkyl with from 1 to 4 carbon atoms, preferably —H or methyl. Especially valuable compounds are N-[5-cyano-4(1H)-oxo-1-pyrimidin]acetamide, (2-methoxyethyl)-N-[5-cyano-4-(1H)-oxo-1pyrimidin]aminoformate, methyl-N-[5-cyano-4-(1H)-oxo-1-pyrimidin]aminoformate, ethyl-N-[5-cyano-4(1H)-oxo-1-pyrimidin]aminoformate and phenyl-N-[5- cyano4(1H)-oxo-1- pyrimidin-]aminoformate which, when administered per os to rats at a rate of 10 to 100 mg/kg, produce a pronounced lowering of the uric acid level in the blood.

Synthesis of compounds of formula I from compounds of formula II is effected without, but preferably in, an organic solvent, for example benzene, toluene, xylene, dioxane, dimethylformamide, ethyl acetate or chloroform, but preferably, an alcohol, more particularly methanol, or a solvent mixture while cooling or at an elevated temperature, preferably between 0° and 60° C and, more particularly, at 20° C.

Alternatively, compounds of formula I are synthesized by heating a compound of formula III or a compound of the formula

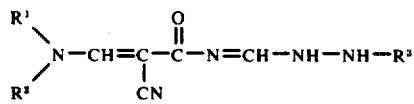

wherein $R^3$ has its previously-ascribed meaning;

$R^1$ is a hydrogen atom (—H) or one of its previously-ascribed meanings; and $R^2$ is one of its previously-ascribed meanings;

or a tautomer or acid addition salt thereof in the absence or presence of inert (oxygen- or nitrogen-free) organic solvent or solvent mixtures, preferably to temperatures of 100° to 180° C; or a compound of formula III or of formula IV is treated with organic or inorganic acid in the absence or presence of organic solvent or solvent mixtures while cooling or at an elevated temperature, preferably at from 0° to 100° C, and more especially at from 70° to 90° C, and conveniently under anhydrous conditions. Suitable organic solvents are hydrocarbons and halogenated hydrocarbons, for example benzene, toluene, xylene and o-dichlorobenzene.

For acid treatment of either a compound of formula II, one of the formula III or one of formula IV (or an acid addition salt or tautomer thereof) suitable acids are hydrogen halides, preferably hydrogen chloride, p-toluenesulfonic acid, formic acid, acetic acid, sulfuric acid or perchloric acid. Acetic acid is preferred for the acid treatment of compounds III and IV. The acid used should be present in at least catalytic quantities for effecting ring closure with compounds of formula II. When ring closure is effected on compounds of formula III or those of formula IV with acid treatment, the acid should also be employed in at least catalytic quantities.

According to a still further method for preparing compounds of formula I, cyanacetamido is reacted with a trialkyl, preferably tri(lower)alkyl, orthoformate [HC(OR)₃] or a dialkoxymethyl, preferably di(lower)alkoxymethyl, ester of an organic carboxylic acid (R'λ COOCH(OR)₂] in the presence of an acid anhydride, and the resulting reaction product is reacted with a hydrazine derivative of the formula $$H_2N—NH—R^3$$

in which $R^3$ has the same meaning as in formula I.

In the last-noted synthesis cyanacetamide is reacted with an trialkyl orthoformate or a dialkoxymethyl ester of an organic carboxylic acid in the presence or preferably in the absence of inert organic solvents, such as benzene, toluene, xylene or o-dichlorobenzene, and the reaction is carried out at room temperature or, preferably, at temperatures between 50° and 150° C, more particularly between 80° and 120° C, or at the boiling temperature of the solvent. The reaction of cyanacetamide with trialkyl orthoformate is preferably carried out in the presence of at least equimolar quantities of acid anhydride. The reaction of cyanacetamide with a dialkoxymethyl ester is preferably carried out in the presence of at least catalytic quantities of acid anhydride, and the orthoester or dialkoxymethyl ester is preferably used in an excess, and more particularly in a twofold to fourfold molar amount relative to the amount of cyanacetamide.

The reaction of the reaction product, obtained from cyanacetamide and trialkyl orthoformate or dialkoxymethyl ester of an carboxylic acid, with the hydrazine derivative $H_2N—NH—R^3$ is preferably carried out in the presence of an inert organic solvent, for example chloroform, benzene, toluene, xylene, dioxane, dimethyl formamide and especially ethyl acetate, while cooling, at room temperature or particularly at an elevated temperature, more particularly between 50° and 150° C, or at the boiling temperature of the solvent.

In a trialkyl orthoformate of the formula $HC(OR)_3$ R denotes an alkyl group with 1 to 7, preferably 1 to 4 carbon atoms, and a trialkyl orthoformate denotes particularly trimethyl- or triethyl orthoformate.

In a dialkoxymethyl ester of organic carboxylic acids of the formula R'COOCH(OR)₂ R' denotes an organic residue, for example aryl, e.g. phenyl, aralkyl, e.g. benzyl, or cycloalkyl, e.g. cyclohexyl, and particularly a hydrogen atom (—H) or an alkyl group with 1 to 7, preferably 1 to 4, carbon atoms; R denotes alkyl with from 1 to 7, preferably 1 to 4, carbon atoms; and a dialkoxymethyl ester of organic carboxylic acids denotes, particularly, dimetho xymethylacetate or diethoxymethylacetate.

Acid anhydrides are anhydrides or mixed anhydrides or organic carboxylic acids, preferably containing from 1 to 4 carbon atoms, for example propionic anhydride or butyric anhydride, and especially acetic anhydride or formic-acetic anhydride. At least when an anhydride, which is different from a mixed anhydride containing the formic residue, is used, it is convenient to use, in addition to the anhydride, an at least catalytic quantity of formic acid to reduce the reaction time.

Based on NMR analysis, the reaction product obtained from the reaction of cyanacetamide with trialkyl orthoformiate or dialkoxymethyl ester of an organic carboxylic acid is a mixture of compounds of the formula

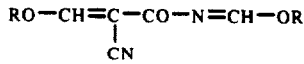

and compounds of the formula

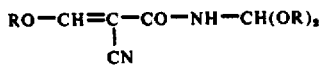   VII or their tautomers, in which R has the previously-ascribed meaning.

The conditions for the described reactions are selected with due consideration of all substituents of the reactants.

The invention also relates to those embodiments wherein (a) a compound (which can be obtained as an intermediate in any particular stage of the method) is used as starting material and additional method steps are carried out, (b) the method is interrupted at some particular stage or (c) a compound used as a starting material is formed under reaction conditions or is used in the form of a reactive derivative, a tautomeric form or a salt.

The new compounds with salt-forming basic groups, such as $NR^5R^6$ groups, are obtained in free-base form or in the form of their salts, depending upon reaction conditions, and these forms are interconverted in a conventional manner.

Salts of the compounds of formula I may be readily or sparingly soluble in water, and the sparingly soluble salts are particularly useful for producing retard forms of such compounds.

The starting materials are preferably materials which lead to the compounds which are indicated to be particularly valuable.

Compounds of formula I and their pharmacologically-compatible salts with organic or inorganic acids possess valuable pharmacological properties and are useful as medicaments. They possess an inhibiting action, novel for such a group of substances, on the enzyme, xanthineoxidase, and concurrently possess extremely low toxicity. These compounds produce a pronounced lowering of the uric acid blood level when administered per se to rats.

Compounds of formula I and their pharmacologically-compatible salts with inorganic and organic acids are therefore valuable therapeutic chemicals, preferably for the treatment of gout, but also for treating coronary insufficiency and with an anti-arrhythmic action. They are also valuable intermediates, for example, for the production of compounds IV, including tautomers thereof. Synthesis of the latter compounds is effected by reacting a compound of formula I with a secondary amine or a cycloimine, such as piperidine, according to the reaction scheme:

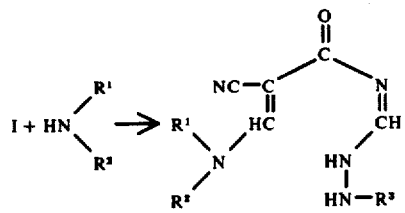   IV wherein $R^1$, $R^2$ and $R^3$ have the meanings previously ascribed to them under formula IV.

This reaction is preferably carried out in the presence of an inert organic solvent, such as benzene, toluene, xylene, dioxane, ethyl acetate, chloroform, dimethyl formamide, or an alcohol, e.g. ethanol or isopropyl alcohol, preferably methanol, while cooling or at an elevated temperature, preferably between 0° and 100° C, and more particularly between 20° and 30° C.

Compounds of formula IV possess an inhibiting action on the enzyme, xanthineoxidase. They, their tautomers and their pharmacologically-accepatable acid addition salts are useful for treating gout by, e.g. administering them orally in unit dosage from to those afflicted with gout.

Medicaments or pharmaceutical compositions which contain one or more compounds of formula I (in a free form or in the form of a pharmacologically-compatible acid addition salt) as active substance can, but need not, contain other pharmacologically-active substance. Such medicaments are produced in a conventional manner by combining the active substance with a pharmaceutical vehicle, such as a filler, a diluent, a correcting agent and/or components conventional for medicaments. The medicaments are produced in a solid dosage form as, e.g., tablets or capsules, or in a liquid form as, e.g., solutions or suspensions. The pharmaceutical vehicle can also contain conventional diluent and tablet-forming additions, such as cellulose powder, maize starch, lactose and talcum, as conventional for such purposes.

The production of a pharmaceutical preparation is carried out in a conventional manner, for example by means of conventional mixing, granulating and coating methods. The pharmaceutical preparations contain from approximately 0.1 to 75%, preferably from 1 to approximately 50%, by weight of the active substance. Administration is enteral, for example oral, or parenteral; individual doses of active substance are between 0.1 and 10, preferably from 0.5 to 5, mg/kg of body weight. For application in human medicine these doses correspond to an individual dose of approximately 10 to 1000, preferably 50 to 500, mg of active substance.

The indicated doses are administered 1 to 4 times daily, for example at mealtimes and/or in the evening. The individual dose, the frequency of administration and the duration of treatment are determined by the nature and severity of the illness.

The invention thus relates to medicaments, particularly for treating gout but also for cardiac insufficiency and arrhythmia. The medicaments are characterized by a content of one or more compounds of formula I in a free form or in the form of pharmacologically-compatible salts.

Without further elaboration, one skilled in the art can, using the preceding description, utilize the present invention. The following specific embodiments are merely illustrative and not limitative of the remainder of the disclosure or of the invention described therein in any way whatsoever.

EXAMPLE 1

Batch for producing 75,000 tablets, each containing 100 mg of active substance

| Components: | |
|---|---|
| 7.500 kg | methyl-N-[5-cyano-4(1H)-oxo-1-pyrimidin] aminoformate (active substance) |
| 4.875 kg | maize starch (4.875 kg) |
| 0.225 kg | amorphous silicic acid |
| 0.300 kg | sodium lauryl sulfate |
| 0.375 kg | polyvinylpyrrolidone |
| 1.200 kg | pectin |
| 0.375 kg | talcum |
| 0.150 kg | magnesium stearate |
| 15.000 kg | |

The active substance, the maize starch, the amorphous silicic acid and the sodium lauryl sulfate are mixed and sieved. This mixture is then moistened with a solution of the polyvinylpyrrolidone in 2.4 l of ethanol and granulated through a sieve with a mesh width of 1.25 mm. The granulate is dried at 40° C and mixed with the pectin, talcum and magnesium stearate. This mixture is then pressed on a rotating machine to form tablets with a weight of 200 mg and a diameter of 8 mm.

Replacing the active substances with the same weight of N-[5-cyano-4(1H)-oxo-1-pyrimidine]acetamide, 5-cyano-1-(2-methoxyethoxy)carbonylamino-4(1H)-pyrimidinone or 5-cyano-1-methoxycarbonylamino-4(1H)-pyrimidinone similarly results in corresponding tablets.

EXAMPLE 2

| Batch for production of 200,000 capsules, each containing 100 mg of active substance | |
|---|---|
| Components: | |
| 20.000 kg | methyl-N-[5-cyano-4(1H)-oxo-1-pyrimidin]aminoformate active substance |
| 0.050 kg | amorphous silicic acid |
| 20,050 kg | |

The active substance in a finely powdered form and the unpressed amorphous silicic acid are well mixed and filled into size 4 hard gelatine capsules.

Replacing the active substance with the same weight of 5-cyano-1-ethoxycarbonylamino-4(1H)-pyrimidinone or 5-cyano-1-phenoxycarbonylamino-4(1H)-pyrimidinone similarly results in corresponding tablets.

EXAMPLE 3

200 Parts by weight of methyl-3-(3-chloro-2-cyano-5-dimethylamino-4-aza-2,4-pentadienylidene)carbazate (for example 0.775 mole) are suspended in 800 parts by weight methanol and mixed at 10° C with 77 parts by weight of concentrated hydrochloric acid (37%). Stirring is carried out for 5 hours at from 5° to 10° C and the produced precipitate is vacuum filtered. Following this, the precipitate is washed with the methanol and dried at 40° C in vacuum to produce 90.5 parts by weight (60% of the theoretical amount) of methyl-N-[5-cyano-4-(1H)-oxo-1-pyrimidine]aminoformate with a decomposition point of 230° C. In a similar manner, using corresponding 3-chloro-2-hydrazonomethyl-4-aza-2,4-pentadienenitriles of formula II, compounds of formula I are obtained wherein $R^3$ is as indicated in the following table:

| $R^3$ | melting point | yield (%) |
|---|---|---|
| —COOC$_2$H$_5$ | 233° decomp. | 45.5 |
| —COOC(CH$_3$)$_3$ | 196° C decomp. | 49 |
| —COO(CH$_2$)$_3$CH$_3$ | 288° C decomp. | 38 |
| —COOCH(CH$_3$)(C$_2$H$_5$) | 233° C decomp. | 61 |
| —COOCH$_2$—C$_6$H$_5$ | 208° C decomp. | 49.5 |
| —COO—C$_6$H$_5$ | 220° C decomp. | 53 |
| —COOCH$_2$—CH$_2$—OCH$_3$ | 217° C decomp. | 63.5 |
| —COO—C$_6$H$_{11}$ (cyclohexyl) | 296° C decomp. | 37.3 |
| —COO(CH$_2$)$_{11}$CH$_3$ | 200° C decomp. | 92 |
| —CONH—C$_6$H$_5$ | 231° C decomp. | 62.7 |
| —COCH$_3$ | 320° C decomp. | 56 |
| —COO(CH$_2$)$_2$OCH$_2$—CH=CH$_2$ | 200° C | 49.3 |
| —COO(CH$_2$)$_2$O—CH(CH$_3$)$_2$ | 222°–223° C | 75 |
| —CO—C$_6$H$_4$—OCH$_3$ | >300° C | 11.7 |

EXAMPLE 4

100 g of methyl-3-(3-chloro-2-cyano-5-dimethylamino-4-aza-2,4-pentadienylidene)carbazate (0.39 mole) and 139 ml of 5.6 molar methanolic hydrochloric acid (0.78 mole) are stirred for 20 hours at 20° C. The resulting precipitate is vacuum filtered, washed with some methanol and dried at 40° C in vacuum. 48.7 g (64.5% of the theoretical amount) of methyl-N-[5-cyano-4(1H)-oxo-1-pyrimidin]-aminoformate are thus obtained with a decomposition point of 230° C.

In a similar manner ethyl-N-[5-cyano-4(1H)-oxo-1-pyrimidin]aminoformate is produced from ethyl-3-(3-chloro-2-cyano-5-dimethylamino-4-aza-2,4-pentadienylidene)carbazate.

EXAMPLE 5

5 Parts by weight of methyl-3-(3-chloro-2-cyano-5-dimethylamino-4-aza-2,4-pentadienylidene)carbazate (for example 19.5 m moles) are suspended in 30 parts by weight of absolute methanol and mixed at 20° C with 1.7 parts by weight of dried p-toluensulfonic acid (for example 10 m moles). After 2 hours cooling is carried out with ice water. Following this, the obtained precipitate is vacuum filtered, washed with methanol and dried at 40° C in vacuo.

2.3 parts by weight of methyl-N-[5-cyano-4(1H)-oxo-1-pyrimidin]aminoformate (61% of the theoretical amount) are obtained with a decomposition point of 230° C.

Following the same procedure and replacing the methyl-3-(3-chloro-2-cyano5-dimethylamino-4-aza-2,4-pentadienylidene)carbazate by an equivalent of 3-chloro-5-dimethylamino-2-formylhydrazonomethyl-4-aza-2,4-pentadidenenitrile or of 3-chloro-5-dimethylamino-2-ethylcarbonylhydrazonomethyl-4-aza-2,4-pentadienenitrile results in the similar preparation of the corresponding compound of formula I.

EXAMPLE 6

5 Parts by weight of methyl-3-(3-chloro-2-cyano-5-dimethylamino-4-aza-2,4-pentadienylidene)carbazate (for example 19.5 m moles) are suspended in 22 parts by weight of methanol and mixed with 2.8 parts by weight of perchloric acid (70%) (for example 19.5 m moles). Stirring is carried out for 2 hours and is followed by cooling to 10° C. The thus-obtained precipitate is vacuum filtered, washed with methanol and dried at 40° C in vacuo.

2.1 parts by weight of methyl-N-[5-cyano-4(1H)-oxo-1-pyrimidin]aminoformate (56% of the theoretical amount) are obtained with a decomposition point of 230° C.

Following the same procedure and replacing the methyl-3-(3-chloro-2-cyano-5-dimethylamino-4-aza-2,4-pentadienylidene)carbazate with an equivalent of 3-chloro-5-dimethylamino-2-n- or iso-propylcarbonylhydrazonomethyl-4-aza-2,4-pentadienentrile results in the similar preparation of the corresponding compound of formula I.

EXAMPLE 7

5 Parts by weight of methyl-3-(3-chloro-2-cyano-2-cyano-5-dimethylamino-4-aza-2,4-pentadienylidene)-carbazate (for example 19.5 m moles) are suspended in 35 parts by weight of methanol and mixed with 2 parts by weight of concentrated sulfuric acid. Stirring is carried out for 3.5 hours at 20° C and is followed by cooling with ice water and vacuum filtering of the resulting precipitate. After washing with methanol and drying at 40° C in vacuo, 2.2 parts by weight of methyl-N-[5-cyano-4(1H)-oxo-1-pyrimidin aminoformate are obtained (58.2% of the theoretical amount) with a decomposition point of 230° C.

Following the same procedure and replacing the methyl 3-(3-chlor0-2-cyano-5] -diethylamino-4-aza-2,4-pentadienylidene)carbazate with an equivalent of 3-chloro-5-diemthylamino-2-heptylcarbonylhydrazonomethyl-b 4-aza-2,4pentadienentirle or of 3-chloro-5-dimethylamino-2-methoxy or phenoxy-acetohydrazonomethyl-4-aza-2,4-pentadienenitrile results is the similar preparation of the corresponding compound of formula I.

EXAMPLE 8

10 Parts by weight of methyl-3-(2-cyano-3-formylamino-3-hydroxyallylidene) carbazate (for example 47.2 m moles) are heated for 15 minutes in 15 parts by weight of glacial acetic acid on a boiling water bath. On cooling, 6 parts by weight of methyl-N-[5-cyano-4(1H)-oxo-1-pyrimidin]aminoformate (65.6% of the theoretical amount) are obtained with a decomposition point of 230° C.

Following the same procedure and replacing the methyl-3-(2-cyano-3-formylamino-3-hydroxyallylidene)carbazate with an equivalent of 5-dimethylamino-3-hydroxy-2-cyclohexyl- or 4-methoxyphenyl-carbonylhydrazonomethyl-4-aza-2,4-pentadienenitrile results in the similar preparation of the corresponding compounds of formula I.

EXAMPLE 9

5 Parts by weight of methyl-3-(2-cyano-3-formylamino-3-hydroxyallylidene) carbazate for example 23.6 m moles) are heated for 90 minutes on an oil bath at 160° C. The residue is heated with 20 ml methanol at reflux temperature and filtered. After drying, 4.25 parts by weight of methyl-N-[5-cyano-4(1H)-oxo-1-pyrimidine]aminoformate (93% of the theoretical amount) are obtained with a decomposition point of 230° C.

Following the same procedure and replacing the methyl-3-(2-cyano-3-formylamino-3-hydroxyallylidene)carbazate with an equivalent of 5-dimethylamino-3-hydroxy-2-trifluoromethylphenyl- or 4-cyanophenyl-carbonylhydrazonomethyl-4-aza-2,4-pentadienenitrile results in the similar preparation of the corresponding compounds of formula I.

In a similar manner, starting from the corresponding 2-hydrazonomethyl-3-hydroxy-4-aza-2,4-pentadienenitriles of formula III (A=H, B=OH), the following 4(1H)-pyrimidinones of formula I are produced:

| R³ | melting point | yield (%) |
|---|---|---|
| —COC₂H₅ | >300° C | 28.6 |
| —COC₃H₇(n) | 240° C | 10.8 |
| —COCH(CH₃)₂ | >300° C | 38 |
|  | >300° C | 63.5 |

EXAMPLE 10

5 Parts by weight of methyl-3-(2-cyano-3-formylamino-3:hydroxyallylidene) carbazate (for example 23.6 m moles) are suspended in 150 parts by weight of xylene and heated for 90 minutes at 150° C. After cooling, vacuum filtration and washing with methanol, drying is carried out at 40° C in vacuo.

4.5 parts by weight of methyl-N-[5-cyano4(1H)-oxo-1-pyrimidin]aminoformate (98% of the theoretical amount) are thus obtained with a decomposition point of b 230° C.

Following the same procedure and replacing the methyl -3-(2-cyano-3-formylamino-3-hydroyallylidene)carbazate with an equivalent of 5-dimethylamino-3-hydroxy-2-dimethylamino(methyl or ethyl)carbonylhydrazonomethyl-4-aza-2,4-pentadieneitrile results in the similar preparation of the corresponding compounds of formula I.

EXAMPLE 11

10 g of methyl-3-(2-cyano-3-hydroxy-5-diethylamino-4-aza-2,4-pentadienylidene)carbazate are heated for 1 hour in 50 ml of glacial acetic acid at 90° C. After cooling and vacuum filtering, washing is carried out with methanol. After drying, 6.51 g of methyl-N-[5-cyano-4(1H)-oxo-1-pyrimidin]aminoformate (89.3% of the theoretical amount) are obtained with a decomposition point of 230° C.

Following the same procedure and replacing the methyl-3-(2-cyano-3-hydroxy-5-diethylamino-4-aza-2,4-pentadienylidene)carbazate by an equivalent of 5-dimethylamino-3-hydroxy-2-pyrrolidinocarbimidohydrazonomethyl-4-aza-2,4-pentadieneitrile results in the similar preparation of the corresponding compound of formula I.

EXAMPLE 12

7.3 g methyl-3-(2-cyano-3-hydroxy-5-pyrrolidine-1-yl-a4-aza-2,4-pentadoenylidene)carbazate are heated for 1 hour in 40 ml of glacial acetic acid at 90° C. The resulting white precipitate is vacuum filtered, washed with methanol and dried. 4.6 g (86% of the theoretical amount) of methyl-N-[5-cyano-4(1H)-oxo-1-pyrimidin]aminoformate are thus obtained with a decomposition point of 230° C.

Following the same procedure and replacing the methyl-3-(2-cyano-3-hydroxy-5-pyrrolidine-1-yl-4-aza-2,4-pentadienylidene)carbazate by an equivalent of 5-dimethylamino-3-hydroxy-2-morpholino-hydrazonomethyl-4-aza-2,4-pentadienenitrile results in the similar preparation of the corresponding compound of formula I.

EXAMPLE 13

4.8 of 2-morpholinomethylen-3-oxo-4-aza-5-(N'-acetylhydrazino)-4-pentenenitrile are heated with 25 ml of glacial acetic acid in a boiling water bath for 10 minutes. After cooling, the precipitate is filtered off.

2.4 g of N-[5-cyano-4(1H)-oxo-1-pyrimidin]acetamide (77% of the theoretical amount) are thus obtained with a melting point of 320° C (decomp.).

The starting material is obtained, e.g., in the following manner: 5 g of 3-morpholino-2-cyanoacrylamide, 12.3 g of triethyl orthoformate, 8.45 g of acetic anhydride and 1.3 g of formic acid are heated at 100° C for 1 hour. After evaporation in vacuo the residue is dissolved in 30 ml of ethyl acetate and filtered. The filtrate is stirred with 2.5 g of acetyl hydrazine at room temperature for 30 minutes. 5.1 g of 2-morpholinomethylen-3-oxo-4-aza-5-(N'-acetylhydrazino)-4-pentenenitrile (70% of theoretical amount) are thus obtained with a melting point of 243° C.

EXAMPLE 14

10 g of cyanacetamide, 70.6 g of triethyl orthoformate and 56 ml of acetic anhydride are heated at 100° C for 5.5 hours. After evaporation in vacuo the residue [yellow oil, $R_f = 0.48$, (TCL, silicagel neutral, chloroform/acetonitrile = 6 / 4)] is dissolved in 70 ml of ethyl acetate and filtered. After adding 8.8 g of acetyl hydrazine thereto, the resulting mixture is refluxed for 30 minutes.

9 g (after purification, 6.5 g) of N-[5-cyano-4(1H)-oxo-1-pyrimidin]acetamide (30.6% of the theoretical amount) are thus obtained with a melting point of 320° C (decomp.).

EXAMPLE 15

3 g of cyanacetamide, 17.5 g of diethoxymethyl acetate and 11 g of acetic anhydride are heated at 100° C for 1.5 hours. After evaporation in vacuo the reaction mixture is dissolved in 30 ml of ethyl acetate and filtered. After addition of 2.7 g of acetyl hydrazine the resulting mixture is refluxed for 20 minutes. 3.3 g (after purification, 3 g) of N-[5-cyano-4(1H)-oxo-1-pyrimidin]acetamide are thus obtained with a melting point of 320° C (decomp.).

What is claimed is:

1. A compound which is characterized by physiological activity, pharmaceutical acceptability, xanthineoxidase-inhibitory utility and a structure which has a (1H)-pyrimidine nucleus that is (organic-acid-acyl)amino substituted in the 1-position, unsubstituted in the 2- and 6-positions, oxo substituted in the 4-position and cyano substituted in the 5-position; the organic acid of the organic-acid acyl being a diazinoheterocyclic-free carbonic or carboxylic acid, a carbon atom of which is directly bound to the amino nitrogen.

2. A compound according to claim 1 which is further characterized by low toxicity and freedom from substitution in the 3-position.

3. A physiologically-active and pharmaceutically-acceptable 1-acylamino-5-cyano-4(1H)-pyrimidinone of the formula

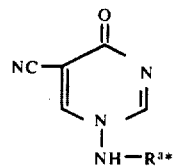

wherein
$R^3$ is $-C(O)-R^4$, $-C(O)-O-R^4$ or $-C(O)-N(R^5)R^6$;
$R^4$ is —H, alkyl having from 1 to 14 carbon atoms, alkenyl having up to 14 carbon atoms, alkynyl having up to 14 carbon atoms, substituted or unsubstituted alkoxyalkyl having from 2 to 13 carbon atoms, substituted or unsubstituted alkenyloxyalkyl having up to 13 carbon atoms, substituted or unsubstituted cycloalkyl having from 3 to 6 ring carbon atoms, substituted or unsubstituted phenyl, nuclearly-substituted or unsubstituted phen(lower-)alkyl; any substituent of, substituted alkoxyalkyl, substituted alkenyloxyalkyl or substituted cycloalkyl being methyl; and any substituent of substituted phenyl or substituted phenalkyl being lower alkyl, lower alkoxy, alkoxycarbonyl with from 2 to 5 carbon atoms, halo, trifluoromethyl, nitro or cyano;
$R^5$ is —H, lower alkyl, lower alkoxyalkyl, cycloalkyl with from 3 to 6 ring carbon atoms or, together with $R^6$, alkylene having from 2 to 5 carbon atoms or a divalent aliphatic chain having three to five chain members, each of at least two of which is methylene or another lower alkylidene and at least one remaining chain member is, independently, —O— or —S— or —N($R^7$)—;
$R^6$ is —H, lower alkyl, lower alkoxyalkyl, cycloalkyl with from 3 to 6 ring carbon atoms or, together with $R^5$, alkylene having from 2 to 5 carbon atoms or a divalent aliphatic chain having from three to five chain members, each of at least two of which is methylene or another lower alkylidene and at least one remaining chain member is, independently, —O— or —S—.

4. A pharmacologically-active and therapeutically-acceptable compound according to claim 3 wherein:
$R^4$ is —H, alkyl having from 1 to 14 carbon atoms, alkoxyalkyl having 2 to 13 carbon atoms, substituted or unsubstituted cycloalkyl having from 3 to 6 ring carbon atoms, phenyl, substituted phenyl, phenalkyl wherein the alkyl has 1 or 2 carbon atoms, nuclearly-substituted phenalkyl wherein the alkyl has 1 or 2 carbon atoms; any substituent of substituted cycloalkyl being methyl; and any nuclear substituent of substituted phenyl or of substituted phenalkyl being alkyl having from 1 to 4 carbon atoms, alkoxy having from 1 to 4 carbon atoms, alkoxycarbonyl having from 2 to 5 carbon atoms, trifluoromethyl, nitro or cyano;

$R^5$ is —H, alkyl having from 1 to 4 carbon atoms, alkoxyalkyl having 2 or 3 carbon atoms, cycloalkyl having from 3 to 6 ring carbon atoms or, together with $R^6$, pentamethylene, 3-oxapentamethylene or 3-thiapentamethylene; and $R^6$ is —H, alkyl having from 1 to 4 carbon atoms, alkoxyalkyl having 2 or 3 carbon atoms, cycloalkyl having from 3 to 6 ring carbon atoms or, together with $R^5$, pentamethylene, 3-oxapentamethylene or 3-thiapentamethylene.

5. A pharmacologically-active and physiologically-compatible compound according to claim 3 which is of the formula

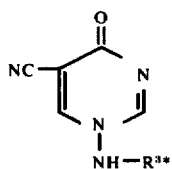

wherein
$R^{3=}$ is —CO—$R^{4=}$, —CO—O$R^{4=}$ or —CO—N($R^{5=}$)$R^{6=}$;

$R^{4=}$ is alkyl having from 1 to 14 carbon atoms, alkoxyalkyl having from 2 to 13 carbon atoms, alkenyloxyalkyl) having up to 13 carbon atoms, substituted or unsubstituted phenyl, nuclearly-substituted or unsubstituted benzyl or substituted or unsubstituted cycloalkyl having from 3 to 6 ring carbon atoms; any substituent of substituted cycloalkyl being methyl; and any substituent of substituted phenyl or substituted benzyl being lower alkyl, lower alkoxy, alkoxycarbonyl with from 2 to 5 carbon atoms, halo, trifluoromethyl, nitro or cyano; and each of $R^{5=}$ and $R^{6=}$ is, independently, —H or alkyl having from 1 to 4 carbon atoms.

6. A therapeutically-active and pharmaceutically-acceptable compound according to claim 5 wherein $R^{4=}$ is alkyl having from 1 to 7 carbon atoms, alkoxyalkyl having from 2 to 6 carbon atoms, substituted or unsubstituted cyclohexyl, phenyl or benzyl; and any substituent of substituted cyclohexyl being methyl; and each of $R^{5=}$ and $R^{6=}$ is, independently, —H or methyl.

7. A pharmaceutically-active and physiologically-acceptable compound according to claim 5 wherein $R^{3=}$ is —CO—$R^{4=}$ or —CO—O$R^{4=}$.

8. The compound according to claim 1 which is N-[5-cyano-4(1H)-oxo-1-pyrimidine]acetamide.

9. The compound according to claim 1 which is (2-methoxyethyl)-N-[5-cyano-4(1H)-oxo-1-pyrimidine]aminoformate.

10. The compound according to claim 1 which is methyl-N-[5-cyano-4(1H)-oxo-1-pyrimidine]aminoformate.

11. The compound according to claim 1 which is ethyl-N-[5-cyano-4(1H)-oxo-1-pyrimidine]aminoformate.

12. The compound according to claim 1 which is phenyl-N-[5-cyano-4(1H)-oxo-1-pyrimidine]aminoformate.

13. A compound according to claim 3 wherein $R^3$ is —C(O)—$R^4$.

14. A compound according to claim 3 wherein $R^3$ is —C(O)—O—$R^4$.

15. A compound according to claim 3 wherein $R^3$ is —C(O)—N($R^5$)$R^6$.

16. A medicament composition in dosage form which contains, as a pharmacologically-active component thereof, an effective amount of at least one compound according to claim 1 and pharmaceutical vehicle or diluent therefor.

17. A pharmaceutically-acceptable composition which contains a total of from about 0.1 percent to about 75 percent by weight of at least one pharmacologically-active compound according to claim 1 and pharmaceutical vehicle for diluent therefor.

18. A composition according to claim 17 which contains a total of from 1 to 50 percent by weight of the pharmacologically-active compound.

19. A method which comprises administering an effective amount of a medicament composition according to claim 17 to a subject afflicted with gout.

20. The compound according to claim 3, wherein $R^3$ is —CHO.

21. A medicament composition according to claim 16 for treating gout and having an effective concentration and amount of the pharmacologically-active component.

22. A medicament composition according to claim 16 for treating cardiac insufficiency and having an effective concentration and amount of the pharmacologically-active component.

23. A medicament composition according to claim 16 for treating arrhythmia and having an effective concentration and amount of the pharmacologically-active component.

* * * * *